United States Patent [19]

Bhore et al.

[11] Patent Number: 5,260,501

[45] Date of Patent: * Nov. 9, 1993

[54] CATALYTIC OLIGOMERIZATION PROCESS USING MODIFIED MESOPOROUS CRYSTALLINE MATERIAL

[75] Inventors: Nazeer A. Bhore, Wilmington, Del.; Ivy D. Johnson, Medford, N.J.; Kathleen M. Keville, Beamount, Tex.; Quang N. Le; Grant H. Yokomizo, both of Cherry Hill, N.J.

[73] Assignee: Mobil Oil Corporation, Fairfax, Va.

[ * ] Notice: The portion of the term of this patent subsequent to Jul. 28, 2009 has been disclaimed.

[21] Appl. No.: 920,944

[22] Filed: Jul. 28, 1992

Related U.S. Application Data

[63] Continuation-in-part of Ser. No. 718,893, Jun. 21, 1991, Pat. No. 5,134,243.

[51] Int. Cl.$^5$ .............................. C07C 2/12
[52] U.S. Cl. .................... 585/533; 585/520; 585/530
[58] Field of Search .................. 585/533, 520, 530

[56] References Cited

U.S. PATENT DOCUMENTS

| | | | |
|---|---|---|---|
| 5,100,533 | 3/1992 | Le et al. | 585/649 |
| 5,105,051 | 4/1992 | Pelrine et al. | 585/533 |
| 5,134,242 | 7/1992 | Le et al. | 585/533 |
| 5,134,243 | 7/1992 | Bhore et al. | 585/530 |
| 5,191,134 | 3/1993 | Le et al. | 585/467 |

Primary Examiner—Anthony McFarlane
Attorney, Agent, or Firm—Alexander J. McKillop; Malcolm D. Keen; L. G. Wise

[57] ABSTRACT

A novel oligomerization catalyst and process for upgrading olefins employing new synthetic catalyst of ultra-large pore crystalline material. The new crystalline material exhibits unusually large sorption capacity demonstrated by its benzene adsorption capacity of greater than about 15 grams benzene/100 grams at 50 torr and 25° C., a hexagonal electron diffraction pattern that can be indexed with a $d_{100}$ value greater than about 18 Angstrom Units and a hexagonal arrangement of uniformly sized pores with a maximum perpendicular cross section of at least about 13 Angstrom units; and the porous crystalline material is impregnated with at least one oligomerization promoting metal, such as Groups VIIIA metals, preferably nickel.

The new process is provided for catalytic oligomerization of olefin feedstock which comprises contacting the feedstock under catalytic conversion conditions with the metal-modified acid metallosilicate solid catalyst having the structure of MCM-41 with hexagonal honeycomb lattice structure consisting essentially of uniform pores in the range of about 20 to 100 Angstroms. The oligomerization reaction is very selective, especially when conducted at temperature of 60° to 120° C. Low severity reaction permits excellent conversion of lower olefins at pressure of about 100–13,000 kPa range and moderate space velocity.

23 Claims, No Drawings

CATALYTIC OLIGOMERIZATION PROCESS USING MODIFIED MESOPOROUS CRYSTALLINE MATERIAL

CROSS-REFERENCE TO RELATED APPLICATIONS

This application is a continuation-in-part of U.S. Pat. application Ser. No. 07/718,893, filed Jun. 21, 1991, now U.S. Pat. No. 5,134,243 incorporated herein by reference.

FIELD OF THE INVENTION

This invention is directed to a catalytic conversion employing a catalyst composition comprising synthetic ultra-large pore crystalline material. In particular it relates to oligomerization of olefins with a nickel-modified catalyst to produce heavier hydrocarbons.

BACKGROUND OF THE INVENTION

Recent work in the field of olefin upgrading has resulted in catalytic processes for converting lower olefins to heavier hydrocarbons. Particular interest is shown in a technique wherein gasoline and/or distillate range hydrocarbons can be synthesized over ZSM-5 type medium pore zeolite catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3^+$ olefins to mainly aliphatic hydrocarbons. In a related manner, U.S. Pat. Nos. 4,150,062, 4,211,640 and 4,717,782 (Garwood et. al.) disclose a process for converting olefins to gasoline components.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}^+$ aliphatic product. Lower olefinic feedstocks containing $C_2$-$C_8$ alkenes may be converted; however, the distillate mode conditions of the prior art do not convert a major fraction of ethylene. A typical reactive feedstock consists essentially of $C_3$-$C_6$ mono-olefins, with varying amounts of nonreactive paraffins and the like being acceptable components.

While low temperature oligomerization is known, prior conventional catalysts have not shown sufficient activity below about 200° C. to be practical in industrial applications. The advantages of low severity oligomerization with medium pore zeolites have been described by Avidan et. al. in U.S. Pat. Nos. 4,746,762 and 4,873,385. It is generally understood that low temperature oligomerization can be selective to produce incremental oligomers which have molecular weights as multiples of the monomers, such as isomeric propene oligomers consisting essentially of $C_6$, $C_9$, $C_{12}$, etc.

These reactions are selective without significant cracking of the desired product; however, the relative inactivity of prior art catalysts has prevented development of low temperature processes.

It is an object of this invention to provide an improved process for catalytic oligomerization of an olefinic feedstock which comprises contacting said feedstock under low severity catalytic conversion conditions with a novel Ni-modified acid solid catalyst having ultra-large pores and exceptionally high oligomerization activity at low temperature.

SUMMARY OF THE INVENTION

The present invention provides a process for catalytic oligomerization of olefins, such as propene, hexenes, 1-decene, etc., which comprises contacting the feedstock under oligomerization conditions with inorganic, porous, non-layered crystalline phase mesoporous catalyst material exhibiting, after calcination, an X-ray diffraction pattern with at least one peak at a d-spacing greater than about 18 Angstrom units and having a benzene adsorption capacity greater than 15 grams of benzene per 100 grams of said material at 50 torr and 25° C.; said catalyst material having active Bronsted acid sites and containing at least one non-framework oligomerization promoting metal component, such as impregnated nickel or other IUPAC Periodic Group VIIIA metal.

The preferred catalyst material has a hexagonal arrangement of uniformly-spaced pores with at least 13 Angstroms diameter, and hexagonal electron diffraction pattern that can be indexed with a $d_{100}$ value greater than 18 Angstrom units; and is a metallosilicate comprising tetrahedrally coordinated Al, Ga or Fe atoms. The most preferred mesoporous catalyst material consists essentially of metallosilicate having the structure of MCM-41, with uniformly distributed honeycomb pores in the 20-100 Angstrom size range. Typical oligomerization reaction temperature is about 40° to 250° C. (preferably below 63° C.), with pressure in the 100-13,000 kPa range; and weight hourly space velocity, based on active catalyst of about 0.1-5/hr WHSV.

DESCRIPTION OF SPECIFIC EMBODIMENTS

The present invention is particularly useful for upgrading $C_2$-$C_6$ lower olefins to heavier hydrocarbons, such as $c_6$-$C_{20}+$ gasoline and distillate fuel product. It is useful in oligomerizing alpha-olefins to make $C_{30}+$ lubricants, for instance by reacting 1-decene to make its trimer, etc. Numerous mono-olefins, including ethene, propene, n-butenes, isobutene, pentenes, hexenes, mixtures thereof, etc., can be reacted selectively in aliphatic hydrocarbon feedstocks. An advantage of the present process is reaction selectivity, such that non-olefinic products can be avoided as reaction by-products, due to the substantial absence of dehydrogenation, cyclization and alkane formation. However, the feedstocks may contain non-deleterious amounts of paraffins, naphthenes, aromatics.

Reaction temperature for oligomerization may vary widely. Below 40° C. the reaction may be too slow and above 250° C. selectivity may be lost for some products. The preferred range is about 40° to 250° C., especially 80° to 200° C. Pressure can also vary greatly from sub-atmospheric to very high pressures (e.g. 10-20,000 kPa), with many process reactions taking place in the 100-13,000 kPa range. By contrast with medium pore zeolites, it has been found that increasing pressure for a given feedstock does not result in higher molecular weight products. This is unexpected behavior for one skilled in the art of zeolitic catalysis. For instance, in propylene oligomerization the distribution of higher incremental oligomers falls dramatically above about 5000 kPa (700 psig) with increased selectivity to hexene and nonene isomers. The reaction may be conducted in the gas phase, liquid phase or dense phase.

Industrial application of the new process will ordinarily require at least 50% conversion of feedstock, preferably about 80–100%, and such conversion can be obtained with continuous reactor operation using fixed bed, fluidized bed, moving bed, slurry reactor, etc. Typical space velocities, based on active catalyst are in the range of about 0.1-5/hr WHSV, preferably 0.5-2.

Catalyst Synthesis and Composition

Recent developments in catalyst technology have provided a group of mesoporous siliceous materials having novel pore geometry. These materials are characterized by substantially uniform hexagonal honeycomb microstructure, with uniform pores having a cell diameter greater than 13 Angstrom units, (preferably in the mesoporous range of about 20–100A). Most prominent among these ultra-large pore size materials is a new metallosilicate called MCM-41, which is usually synthesized with Bronsted acid active sites by incorporating a tetrahedrally coordinated trivalent element, such as Al, Ga, B, or Fe, within the silicate framework. Aluminosilicate materials of this type are thermally and chemically stable, properties favored for acid catalysis; however, the advantages of mesoporous structures may be utilized by employing highly siliceous materials or crystalline metallosilicate having one or more tetrahedral species having varying degrees of acidity. In addition to the preferred aluminosilicates, the gallosilicate, ferrosilicate and borosilicate materials may be employed. Although matrices may be formed with the germanium analog of silicon, these are expensive and generally no better than the metallosilicates.

MCM-41 crystalline structure is readily recognized by its spectrographic characteristics, such as electron micrograph, X-ray diffraction pattern, absorption properties, etc., as described in U.S. Pat. Nos. 5,098,684 and 5,102,643 (Kresge, Leonowicz, Roth and Vartuli); and a preferred synthesis is described in U.S. Pat. No. 5,057,296 Beck, incorporated by reference.

The catalysts preferred for use herein include the ultralarge pore crystalline aluminosilicates having a silica-to-alumina ratio of about 5:1 to 1000:1 and significant Bronsted acid activity. Acid activity may be measured by acid cracking activity or ammonia absorption properties, such as temperature programmed desorption.

In discussing tetrahedrally coordinated metal oxides of the zeolitic type, it is understood that adjacent metal sites in the matrix are linked by oxygen (i.e., —Si—O—Si—). the honeycomb microstructure of MCM-41 and related mesoporous materials may include several moieties interconnected in a three dimensional matrix or lattice having large hexagonal channels therein forming the ultralarge pores of the catalyst. The repeating units forming the large ring structure of the lattice vary with pore size. A typical catalyst component having Bronsted acid sites consists essentially of crystalline aluminosilicate having the structure of MCM-41, optionally containing 5 to 95 wt. % silica, clay and/or alumina binder. These siliceous materials may be ion-exchanged or impregnated with one or more suitable metals, such as Pd, Ni, Co and/or other metals of Periodic Group VIIIA (IUPAC). Metal incorporation techniques are described by Garwood et. al. in U.S. Pat. No. 4,717,782 and in copending U.S. patent applications Ser. Nos. 07/734,998 and 07/734,990, filed Jul. 24, 1991.

The inorganic, non-layered mesoporous crystalline catalytic material employed in this invention has the following composition:

$$M_{n/q}(W_a X_b Y_c Z_d O_h);$$

wherein W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and $(a+b+c+d)=1$.

A preferred embodiment of the above crystalline material is when $(a+b+c)$ is greater than d, and $h=2$. A further embodiment is when a and $d=0$, and $h=2$.

In the as synthesized form, the material of this invention has a composition, on an anhydrous basis, expressed empirically as follows:

$$rRMM_{n/q}(W_a X_b Y_c Z_d O_h);$$

wherein R is the total organic material not included in M as an ion, and r is the coefficient for R, i.e. the number of moles or mole fraction of R.

The M and R components are associated with the material as a result of their presence during crystallization, and are easily removed or, in the case of M, replaced by post-crystallization methods hereinafter more particularly described. To the extent desired, the original M, e.g. sodium or chloride, ions of the as-synthesized material of this invention can be replaced in accordance with techniques well known in the art, at least in part, by ion exchange with other ions. Preferred replacing ions include metal ions, hydrogen ions, hydrogen precursor, e.g. ammonium, ions and mixtures thereof. Particularly preferred ions are those which tailor the catalytic activity for mono-olefinic hydrocarbon oligomerization reaction. These include hydrogen and metals of Group VIIIA (e.g. Ni) of the IUPAC Periodic Table of the Elements.

The crystalline (i.e. meant here as having sufficient order to provide a diffraction pattern such as, for example, by X-ray, electron or neutron diffraction, following calcination with at least one peak) mesoporous material of this invention may be characterized by its heretofore unknown structure, including extremely large pore windows, and high sorption capacity. The term "mesoporous" is used here to indicate crystals having uniform pores within the range of from about 13 Angstroms to about 200 Angstroms. The materials of this invention will have uniform pores within the range of from about 13 Angstroms to about 200 Angstroms, more usually from about 15 Angstroms to about 100 Angstroms. For the purposes of this application, a working definition of "porous" is a material that adsorbs at least 1 gram of a small molecule, such as Ar, $N_2$, n-hexane or cyclohexane, per 100 grams of the solid.

The material of the present invention can be distinguished from other porous inorganic solids by the regularity of its large open pores, whose pore size more nearly resembles that of amorphous or paracrystalline materials, but whose regular arrangement and uniformity of size (pore size distribution within a single phase of, for example, ±25%, usually ±15% or less of the average pore size of that phase) resemble more those of crystalline framework materials such as zeolites. The material appears to have a hexagonal arrangement of large open channels that can be synthesized with open internal diameters from about 13 Angstroms to about 200 Angstroms. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as +25% random deviation from the average repeat distance between adjacent channels still clearly give recognizable images of the present ultra-large pore materials. Comparable variations are also observed in the $d_{100}$ values from the electron diffraction patterns.

The most regular preparations of the material of the present invention give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100} = a_0\sqrt{3}/2$. This $d_{100}$ spacing observed in the electron diffraction patterns corresponds to the d-spacing of a low angle peak in the X-ray diffraction pattern of the material. The most highly ordered preparations of the material obtained so far have 20–40 distinct spots observable in the electron diffraction patterns. These patterns can be indexed with the hexagonal hk0 subset of unique reflections of 100, 110, 200, 210, etc., and their symmetry-related reflections.

In its calcined form, the crystalline material of the invention may be further characterized by an X-ray diffraction pattern with at least one peak at a position greater than about 18 Angstrom Units d-spacing (4.909 degrees two-theta for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials, e.g. silica, and organics may be removed by contact with acid or base or other chemical agents such that the detrital material will be removed without detrimental effect on the crystal of the invention.

More particularly, the calcined crystalline non-layered material of the invention may be characterized by an X-ray diffraction pattern with at least two peaks at positions greater than about 10 Angstrom Units d-spacing (8.842 degrees two-theta for Cu K-alpha radiation), at least one of which is at a position greater than about 18 Angstrom Units d-spacing, and no peaks at positions less than about 10 Angstrom units d-spacing with relative intensity greater than about 20% of the strongest peak. Still more particularly, the X-ray diffraction pattern of the calcined material of this invention will have no peaks at positions less than about 10 Angstrom units d-spacing with relative intensity greater than about 10% of the strongest peak. In any event, at least one peak in the X-ray diffraction pattern will have a d-spacing that corresponds to the $d_{100}$ value of the electron diffraction pattern of the material.

Still more particularly, the calcined inorganic, non-layered crystalline material of the invention is characterized as having a pore size of about 13 Angstroms or greater as measured by physisorption measurements, hereinafter more particularly set forth. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75-100), s=strong (50-74), m=medium (25-49) and w=weak (0-24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the material of the invention, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

The mesoporous composition can be used as a catalyst component in intimate combination with a metal hydrogenating component such as Group VIIIA (e.g. Ni) of the IUPAC Periodic Table of the Elements, rhenium, nickel, cobalt, or a noble metal such as platinum or palladium or mixtures thereof. For the process herein, however, nickel has certain unique properties in oligomer formation that render it a preferred modifying material. Such component can be in the composition by way of co-crystallization, exchanged into the composition to the extent a Group IIIB element, e.g. aluminum, is in the structure, impregnated therein or intimately physically admixed therewith. Such component can be impregnated in the porous crystal by other conventional methods.

The above crystalline material, especially in its metal, hydrogen and ammonium forms can be beneficially converted to another form by thermal treatment (calcination). This thermal treatment is generally performed by heating one of these forms at a temperature of at least 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

The crystalline material of this invention, when employed either as an adsorbent or as a catalyst component in an organic compound conversion process should be dehydrated, at least partially. This can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

The present crystalline material can be prepared by one of several methods, each with particular limitations.

A first method involves a reaction mixture having an $X_2O_3/YO_2$ mole ratio of from 0 to about 0.5, but an $Al_2O_3/SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, hereinafter more particularly described. This first method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, an organic (R) directing agent, hereinafter more particularly described, and a solvent or solvent mixture, such as, for example, $C_1$-$C_6$ alcohols, $C_1$-$C_6$ diols and/or water, especially water, said reaction mixture having a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $Al_2O_3/SiO_2$ | 0 to 0.01 | 0.001 to 0.01 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/$(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.01 to 2.0 | 0.03 to 1.0 | wherein e and f are the weighted average valences of M and R, respectively.

In this method, when no Z and/or W oxides are added to the reaction mixture, the pH is important and must be maintained at from about 9 to about 14. When Z and/or W oxides are present in the reaction mixture, the pH is not narrowly important for synthesis of the present crystalline material. In this, as well as the following methods for synthesis of the present material the $R_{2/f}O/(YO_2+WO+Z_2O_5+X_2O_3)$ ratio is important. When this ratio is less than 0.01 or greater than 2.0, impurity products tend to be synthesized at the expense of the present material.

By adjusting conditions of the synthesis reaction for each method, like temperature, pH and time of reaction, etc., within the above limits, embodiments of the present non-layered crystalline material with a desired average pore size may be prepared. In particular, changing the pH, the temperature or the reaction time may promote formation of product crystals with different average pore size.

Non-limiting examples of various combinations of W, X, Y and Z contemplated for the first and second synthesis methods of the present invention include:

| W  | X  | Y  | Z |
|----|----|----|---|
| —  | Al | Si | — |
| —  | Al | —  | P |
| —  | Al | Si | P |
| Co | Al | —  | P |
| Co | Al | Si | P |
| —  | —  | Si | — | including the combinations of W being Mg, or an element selected from the divalent first row transition metals, e.g. Mn, Co and Fe; X being B, Ga or Fe; and Y being Ge.

An organic directing agent for use in each of the above methods for synthesizing the present material from the respective reaction mixtures is an ammonium or phosphonium ion of the formula $R_1R_2R_3R_4Q^+$, i.e.:

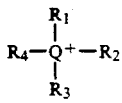

wherein Q is nitrogen or phosphorus and wherein at least one of $R_1$, $R_2$, $R_3$ and $R_4$ is aryl or alkyl of from 6 to about 36 carbon atoms, e.g. —$C_6H_{13}$, —$C_{10}H_{21}$, —$C_{16}H_{33}$ and —$C_{18}H_{37}$, or combinations thereof, the remainder of $R_1$, $R_2$, $R_3$, and $R_4$ being selected from the group consisting of hydrogen, alkyl of from 1 to 5 carbon atoms and combinations thereof. The compound from which the above ammonium or phosphonium ion is derived may be, for example, the hydroxide, halide, silicate, or mixtures thereof. Examples of these directing agents include quaternary compounds, such as cetyltrimethylammonium, cetyltrimethylphosphonium, octadecyltrimethylphosphonium, benzyltrimethylammonium, cetylpyridinium, myristyltrimethylammonium, decyltrimethylammonium, dodecyltrimethylammonium and dimethyldidodecylammonium. Crystal size and crystallization time of the new crystalline material will vary with the nature of the reaction mixture employed and the crystallization conditions.

The crystals prepared by the instant invention can be shaped into a wide variety of particle sizes. Generally speaking, the particles can be in the form of a powder, a granule, or extrudate.

In the examples metric units and parts by weight are employed unless otherwise indicated.

Catalyst Preparation Example 1-A

The following mixture was charged to a five-gallon autoclave:

9600g Cetyltrimethylammonium (CTMA) hydroxide, prepared by contacting a 29 wt % N,N,N-trimethyl-1-hexadecylammonium chloride solution with a hydroxide-for-halide exchange resin, 200 g of sodium aluminate, 4800 g of tetramethylammonium silicate (10% aqueous solution), 1200 g HiSil, a precipitated hydrated silica.

The mixture was crystallized at 100° C. for 20 hours. The mixture had a molar composition in terms of moles per mole $Al_2O_3$:

1.46 moles $Na_2O$
27.8 moles $SiO_2$
5.6 moles $(CTMA)_2O$
3.11 moles $(TMA)_2O$
723.7 moles $H_2O$ The resulting product was recovered by filtration and dried in air at ambient temperature. A sample of the product was calcined at 540° C. for 1 hour in nitrogen, followed by 6 hours in air for characterization.

The calcined product had a surface area of 1220 m$^2$/g and the following equilibrium adsorption capacities in grams/100 grams:

| $H_2O$       | 13.5 |
| Cyclohexane  | >50  |
| n-hexane     | 43.6 |
| Benzene      | 71   |

The product of this example may be characterized as including a very strong relative intensity line at 38.4±2.0 Angstroms d-spacing, and weak lines at 22.6±1.0, 20.0±1.0, and 15.2±1.0 Angstroms.

Catalyst Preparation Example 1-B

The Ni impregnated MCM-41 catalyst was prepared by calcining as-synthesized MCM-41 crystals for six hours at 950° F. in nitrogen followed by 12 hours at 1000° F. in air. The calcined crystals were pelleted and impregnated with a 0.56M aqueous solution of nickel sulfate. The catalyst was air dried for 12 hours at 250° F.. The dried catalyst was subsequently calcined in air at 300° F. for two hours, 575° F. for two hours, and 930° F. for three hours. The finished catalyst contained 3.2 wt % Ni.

Process Example 2

To assess the catalytic properties of MCM-41, experiments are performed in a fixed bed isothermal tubular reactor containing Ni-modified acidic MCM-41. The temperature is varied from about 65° C. to 120° C. (140° F.-250° F.). The pressure is maintained at about 7000 kPa (1000 psig) and the weight hourly space velocity varied between 0.65 and 1.0 (based on active catalyst). Propylene is oligomerized by contact with the MCM-41 catalyst prepared according to the method of Catalyst Examples 1-A and 1-B, pelletized to form solid particles having a size range of about 14/60 mesh.

The product compositions are given in Table A. Included in Table A are the product distributions obtained from MCM-41 and a commercial, homogeneous nickel catalyst, DIMERSOL[1].

COMPARATIVE EXAMPLES

Included in Table A are examples of alternative oligomerization catalysts, including $SiO_2$-bound MCM-41. Reaction conditions are listed for comparison purposes.

TABLE A

| Sample  | Propylene Oligomerization | | | | | | | | |
|---------|------|------|-------|-------|-----|-----|------|------|------|
|         | Temp. °F./°C. | WHSV | Press. psig | Conv. wt. % | \multicolumn{5}{c}{Olefin Selectivity[a]} | | | | |
|         |      |      |       |       | $C_6$ | $C_9$ | $C_{12}$ | $C_{15}$ | $C_{18}$ |
| Unbound | 145/63 | 0.65 | 1000 | 82 | 26 | 46 | 21 | 5 | 2 |

TABLE A-continued

| | | Propylene Oligomerization | | | | | | | |
|---|---|---|---|---|---|---|---|---|---|
| | Temp. | | Press. | Conv. | Olefin Selectivity[a] | | | | |
| Sample | °F./°C. | WHSV | psig | wt. % | $C_6$ | $C_9$ | $C_{12}$ | $C_{15}$ | $C_{18}$ |
| Ni—MCM-41 | 141/61 | 0.65 | 1000 | 27 | 13 | 67 | 16 | 4 | 0 |
| Comparative Examples: | | | | | | | | | |
| SiO$_2$-Bound MCM-41 | 247/120 | 1.0 | 1000 | 94 | 7 | 45 | 33 | 12 | 3 |
| MCM-41 | 233/112 | 1.0 | 1000 | 43 | 11 | 62 | 22 | 4 | 1 |
| DIMERSOL[1] | 86/30 | NA | ~700 | 90 | 80 | 18 | 2 | — | |

[1]Commercial, homogenous process, reference Benedek et al., Hydrocarbon Processing (1980); 59, 143.

The data contained in Table A show that the ultra large pore MCM-41 zeolite exhibits comparable conversion compared with a commercial process for propylene oligomerization. MCM-41 also provides significantly higher $C_9$ and $C_{12}$ hydrocarbon yield for propylene oligomerization.

The present process shows unique advantages for the use of ultra large pore MCM-41 catalyst in olefin oligomerization reactions. Compared to medium pore zeolites, the recently discovered mesoporous MCM-41 catalysts show higher activity and greater selectivity for the formation of trimers and tetramers for propylene oligomerization. The degree of branching can be controlled by varying process variables.

The ability of ultra large pore MCM-41 catalysts to selectively oligomerize olefins, especially propylene, at low temperature (i.e. <100° C.) to trimers and tetramers is unexpected and represents a significant improvement over previous catalysts. The high activity allows for control of branching index by varying the process parameters such as pressure and feed flowrate.

The disclosed catalyst for light olefin oligomerization provides the flexibility to adjust product selectivity and branching index for product use as clean gasoline, diesel fuel, detergents or lubrication fluid. In contrast, ZSM-5 and ZSM-23 catalysts require a significantly higher operating temperature which results in the production of a broad range of hydrocarbons. The high activity of ultra-large pore MCM-41 allows for lower temperature operation which results in selective trimer and tetramer formation and may improve catalyst stability. For propylene oligomerization, MCM-41 provides unique selectivity toward $C_9$ and $C_{12}$ olefinic hydrocarbons which, with subsequent hydrogenation, can be utilized as clean gasoline and diesel fuel components.

We claim:

1. In the process for oligomerizing alkene feedstock by contacting the feedstock with acidic, porous, solid catalyst under oligomerization conditions; the improvement wherein said catalyst comprises an inorganic, porous crystalline phase material having, after calcination, a hexagonal arrangement of uniformly-sized pores having diameters of at least about 13 Angstrom Units and exhibiting a hexagonal electron diffraction pattern that can be indexed with a $d_{100}$ value greater than about 18 Angstrom Units; said porous crystalline phase material containing a catalytically effective amount of nickel.

2. The process of claim 1 wherein said crystalline phase has an X-ray diffraction pattern following calcination with at least one peak whose d-spacing corresponds to the $d_{100}$ value from the electron diffraction pattern.

3. The process of claim 1 wherein said crystalline phase exhibits a benzene adsorption capacity of greater than about 15 grams benzene per 100 grams at 50 torr and 25° C.

4. The process of claim 1 wherein said crystalline phase has a composition expressed as follows:

wherein M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and $(a+b+c+d)=1$.

5. The process of claim 4 wherein the sum $(a+b+c)$ is greater than d, and $h=2$.

6. The process of claim 4 wherein W is divalent first row transition metal or magnesium; X is aluminum, boron, gallium or iron; Y is silicon or germanium; and Z comprises phosphorus.

7. The process of claim 4 wherein W comprises cobalt, X comprises aluminum, Y comprises silicon and Z comprises phosphorus.

8. The process of claim 5 wherein W is a divalent first row transition metal or magnesium; X is aluminum, boron, gallium or iron; Y is silicon or germanium; and Z comprises phosphorus.

9. The process of claim 5 wherein W comprises cobalt, X comprises aluminum, Y comprises silicon and Z comprises phosphorus.

10. The process of claim 4 wherein a and d are 0 and $h=2$; and wherein X aluminum, boron, gallium or iron and Y is silicon or germanium.

11. The process of claim 4 wherein X comprises aluminum and Y comprises silicon.

12. The process of claim 4 wherein original ions are replaced, at least in part, with an ion or a mixture of ions selected from the group consisting of hydrogen and hydrogen precursors metals of Group VIIIA of the IUPAC Periodic Table of the Elements.

13. The process of claim 12 wherein the crystalline material results from thermal treatment.

14. The process of claim 12 wherein said replacing ions comprise hydrogen or a hydrogen precursor.

15. The process of claim 1 wherein said catalyst comprises a matrix.

16. The process of claim 15 wherein said matrix comprises alumina, silica, clay or mixtures thereof.

17. A process for catalytic oligomerization of $C_2$-$C_{12}$ olefin feedstock which comprises contacting said feedstock under catalytic conversion conditions with acid metallosilicate solid catalyst having the structure of MCM-41 with hexagonal honeycomb lattice structure consisting essentially of uniform pores in the range of about 20 to 100 Angstroms and being impregnated with at least one oligomerization promoting metal.

18. The process of claim 17 wherein said metallosilicate comprises tetrahedrally coordinated Al, Ga or F atoms; wherein said oligomerization promoting metal comprises nickel; wherein oligomerization reaction temperature is about 40° to 250° C.; pressure is about 100–13,000 kPa range; and weight hourly space velocity, based on active catalyst is about 0.1–5/hr WHSV, and wherein said oligomerization promoting metal comprises at least one Groups VIII metal of the IUPAC Periodic Table.

19. The process of claim 17 wherein the olefin consists essentially of propene, wherein the oligomerization reaction temperature is not greater than 100° C.; and pressure is maintained above about 5000 kPa to obtain increased selectivity to hexene and nonene isomers.

20. A process for catalytic oligomerization of olefin which comprises contacting said feedstock under catalytic oligomerization conditions with inorganic, porous, non-layered crystalline phase catalyst material exhibiting, after calcination, an X-ray diffraction pattern with at least one peak at a d-spacing greater than about 18 Angstrom units and having a benzene adsorption capacity greater than 15 grams of benzene per 100 grams of said material at 50 torr and 25° C.; said catalyst material having active Bronsted acid sites, and containing non-framework nickel in an amount effective to promote oligomerization of $C_2$–$C_6$ alkenes.

21. The process of claim 20 wherein said catalyst material has a hexagonal arrangement of uniformly-spaced pores with at least 13 Angstroms diameter, and having a hexagonal electron diffraction pattern that can be indexed with a $d_{100}$ value greater than 18 Angstrom units; and wherein said olefin is at least one $C_3$–$C_6$ alkene; and wherein said catalyst consists essentially of metallosilicate which is tetrahedrally coordinated with Al, Ga or Fe atoms, impregnated with about 0.1 to 10 weight percent nickel.

22. The process of claim 20 wherein said catalyst material consists essentially of aluminosilicate having the structure of MCM-41; wherein oligomerization reaction temperature is 40° to 100° C.; pressure is about 100–13,000 kPa range; and weight hourly space velocity, based on active catalyst is about 0.1–5/hr WHSV.

23. The process of claim 20 wherein said catalyst material consists essentially a metallosilicate having hexagonal honeycomb lattice structure consisting essentially of uniform pores in the range of about 20 to 100 Angstroms, and containing about 3 wt % Ni.

* * * * *

UNITED STATES PATENT AND TRADEMARK OFFICE
CERTIFICATE OF CORRECTION

PATENT NO. : 5,260,501

DATED : November 9, 1993

INVENTOR(S) : N. A. Bhore et al.

It is certified that error appears in the above-identified patent and that said Letters Patent is hereby corrected as shown below:

Col. 11, line 50, "the" should be --a--

Col. 12, line 31, insert --a-- before "divalent"

Col. 12, line 46, insert --is-- after "X"

Signed and Sealed this

Thirty-first Day of May, 1994

Attest:

BRUCE LEHMAN

*Attesting Officer*  *Commissioner of Patents and Trademarks*